| United States Patent [19] | [11] Patent Number: 5,064,947 |
| --- | --- |
| Peet et al. | [45] Date of Patent: Nov. 12, 1991 |

[54] SELECTIVE ADENOSINE RESEPTOR COMPOUNDS

[75] Inventors: Norton P. Peet, Cincinnati; Nelsen L. Lentz, West Chester, both of Ohio

[73] Assignee: Merrell Dow Pharmaceuticals Inc., Cincinnati, Ohio

[21] Appl. No.: 544,811

[22] Filed: Jun. 27, 1990

Related U.S. Application Data

[63] Continuation of Ser. No. 330,400, Mar. 29, 1989, abandoned.

[51] Int. Cl.$^5$ .................. C07H 19/06; C07D 487/02; A61K 31/735
[52] U.S. Cl. ....................................... 536/26; 544/251
[58] Field of Search ................ 544/251; 514/267, 46; 536/26

[56] References Cited

U.S. PATENT DOCUMENTS

| 3,830,795 | 8/1974 | Prasad et al. | 260/211.5 |
| 3,830,796 | 8/1974 | Prasad | 536/26 |
| 3,931,401 | 1/1976 | Prasad et al. | 424/180 |
| 4,007,268 | 2/1977 | Voorhees | 424/200 |
| 4,388,308 | 6/1983 | Hamilton | 514/46 |
| 4,728,644 | 3/1988 | Yuki et al. | 544/277 |

FOREIGN PATENT DOCUMENTS

JO1063582 3/1987 Japan ..................... 544/251

OTHER PUBLICATIONS

Spremulli et al., "Hemodynamic . . . ," CA 98: 172756 (1983).
Derwent Abstract 74–60887V.
Derwent Abstract 76–05684X.
Derwent Aabstract 74–32976V.
T. P. Johnston et al., *J. Org. Chem.*, 27, 974 (1962).

*Primary Examiner*—C. Warren Ivy
*Assistant Examiner*—Celia Chang
*Attorney, Agent, or Firm*—Michael J. Sayles

[57] ABSTRACT

Adenosine analogues which act selectively at adenosine receptors and which act in general as adenosine antagonists are disclosed. From in vitro studies it is known that specific physiological effects can be distinguished as a result of this selectivity and that adenosine receptor activity in vitro correlates with adenosine receptor activity in vivo. Pharmaceutical preparations of the subject compounds can be prepared on the basis of the selective binding activity of the compounds disclosed herein which can be expected to enhance certain physiological effects while minimizing others, such as decreasing blood pressure without decreasing heart rate.

20 Claims, No Drawings

SELECTIVE ADENOSINE RESEPTOR COMPOUNDS

This is a continuation of application Ser. No. 330,400, filed Mar. 29, 1989, now abandoned.

FIELD OF THE INVENTION

The present invention relates to a group of compounds which are adenosine analogues and which act selectively at adenosine receptors.

BACKGROUND OF THE INVENTION

The profound hypotensive, sedative, antispasmodic, and vasodilatory actions of adenosine were first recognized over 50 years ago. Subsequently, the number of biological roles proposed for adenosine have increased considerably. The adenosine receptors appear linked in many cells to adenylate cyclase. A variety of adenosine analogues have been introduced in recent years for the study of these receptor functions. Alkylxanthines, such as caffeine and theophylline, are the best known antagonists of adenosine receptors.

Adenosine perhaps represents a general regulatory substance, since no particular cell type or tissue appears uniquely responsible for its formation. In this regard, adenosine is unlike various endocrine hormones. Nor is there any evidence for storage and release of adenosine from nerve or other cells. Thus, adenosine is unlike various neurotransmitter substances.

Adenosine might be compared as a physiological regulator to the prostaglandins. In both cases the enzymes involved in the metabolic formation are ubiquitous and appear to be responsive to alterations in the physiological state of the cell. Receptors for adenosine, like those for prostaglandins, are proving to be very widespread. Finally, both prostaglandins and adenosine appear to be involved with the regulation of functions involving calcium ions. Prostaglandins, of course, derive from membrane precursors, while adenosine derives from cytosolic precursors.

Although adenosine can affect a variety of physiological functions, particular attention has been directed over the years toward actions which might lead to clinical applications. Preeminent has been the cardiovascular effects of adenosine which lead to vasodilation and hypotension but which also lead to cardiac depression. The antilipolytic, antithrombotic and antispasmodic actions of adenosine have also received some attention. Adenosine stimulates steroidogenesis in adrenal cells, again probably via activation of adenylate cyclase. Adenosine has inhibitory effects on neurotransmission and on spontaneous activity of central neurons. Finally, the bronchoconstrictor action of adenosine and its antagonism by xanthines represents an important area of research.

It has now been recognized that there are not one but at least two classes of extracellular receptors involved in the action of adenosine. One of these has a high affinity for adenosine and at least in some cells couples to adenylate cyclase in an inhibitory manner. These have been termed by some as the A-1 receptors. The other class of receptors has a lower affinity for adenosine and in many cell types couples to adenylate cyclase in a stimulatory manner. These have been termed the A-2 receptors.

Characterization of the adenosine receptors has now been possible with a variety of structural analogues. Adenosine analogues resistant to metabolism or uptake mechanisms have become available. These are particularly valuable, since their apparent potencies will be less affected by metabolic removal from the effector system. The adenosine analogues exhibit differing rank orders of potencies at A-1 and A-2 adenosine receptors, providing a simple method of categorizing a physiological response with respect to the nature of the adenosine receptor The blockade of adenosine receptors (antagonism) provides another method of categorizing a response with respect to the involvement of adenosine receptors. It should be noted that the development of antagonists specific to A-1 or A-2 adenosine receptors would represent a major breakthrough in this research field and in the preparation of adenosine receptor selective pharmacological agents having specific physiological effects in animals.

SUMMARY OF THE INVENTION

The present invention relates to compounds having the following general formula

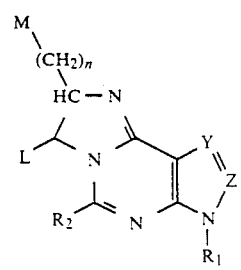

wherein $R_1$ is hydrogen, phenyl or $\beta$-D-ribofuranosyl; $R_2$ is hydrogen, lower alkyl of from 1 to 4 carbon atoms or lower alkoxy of from 1 to 4 carbon atoms; Y is —N= or —CH=; Z is —N= or —CH=, with the proviso that Y and Z cannot be identical; n is an integer from 1 to 3; L is hydrogen or phenyl; and M is phenyl, except when L is phenyl, in which case M is hydrogen or lower alkyl of from 1 to 3 carbon atoms.

DETAILED DESCRIPTION OF THE INVENTION

The lower alkyl groups, as indicated above, contain 1 to 4 carbon atoms and this same definition applies to any use of the term below. Similarly, the lower alkoxy groups, as indicated above, contain 1 to 4 carbon atoms and this definition applies to any use of the terms below. Examples of such alkoxy groups are methoxy, ethoxy, propoxy, and butoxy.

In general, compounds according to the present invention are made by the following procedures. Compounds of the following structure:

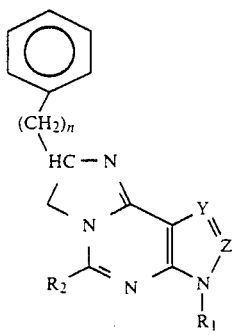

wherein $R_1$ is hydrogen, phenyl or $\beta$-D-ribofuranosyl; $R_2$ is hydrogen, lower alkyl of from 1 to 4 carbon atoms or lower alkoxy of from 1 to 4 carbon atoms; n is an integer from 1 to 3; Y is —N= or —CH=; and Z is —N= or —CH=, with the proviso that Y and Z cannot be identical, can be made by reacting a compound of the structure:

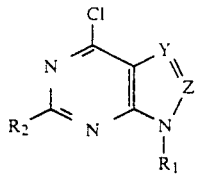

wherein $R_1$ is hydrogen, phenyl or $\beta$-D-ribofuranosyl; $R_2$ is hydrogen or chlorine; Y is —N= or —CH=; and Z is —N= or —CH=, with the proviso that Y and Z cannot be identical, with a compound of the structure:

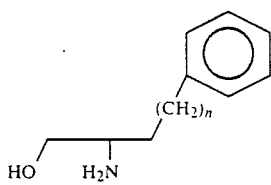

wherein n is an integer from 1 to 3, as described in further detail in the examples below.

The resulting compound of the structure:

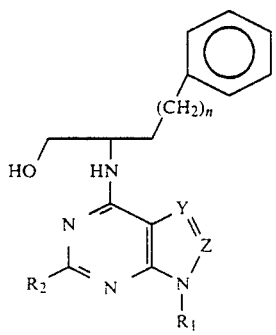

wherein $R_1$ is hydrogen, phenyl or $\beta$-D-ribofuranosyl; $R_2$ is hydrogen or chlorine; Y is —N= or —CH=; Z is —N= or —CH=, with the proviso that Y and Z are not identical; and n is an integer from 1 to 3, can be further reacted with thionyl chloride, or a similar reagent, to produce a compound of the structure;

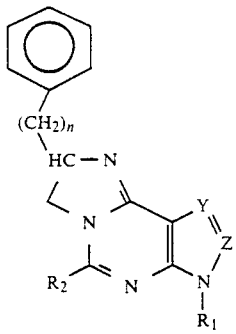

wherein $R_1$ is hydrogen, phenyl or $\beta$-D-ribofuranosyl; $R_2$ is hydrogen or chlorine; Y is —N= or —CH=; and Z is —N= or —CH=, with the proviso that Y and Z cannot be identical.

Furthermore, a compound of the structure shown above wherein $R_2$ is chlorine can be further reacted with a selected alcohol of from 1 to 4 carbon atoms, such as n-propanol, to form a compound of the structure:

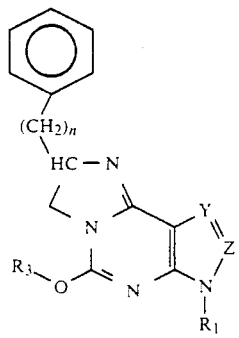

wherein $R_1$ is hydrogen, phenyl or $\beta$-D-ribofuranosyl; $R_3$ is lower alkyl of from 1 to 4 carbon atoms; Y is —N= or —CH=; and Z is —N= or —CH=, with the proviso that Y and Z cannot be identical.

Likewise, compounds of the general formula:

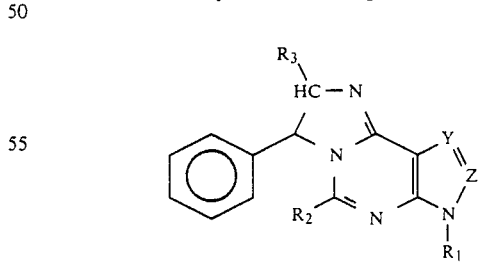

wherein $R_1$ is hydrogen, phenyl or $\beta$-D-ribofuranosyl; $R_2$ is hydrogen, lower alkyl of from 1 to 4 carbon atoms or lower alkoxy of from 1 to 4 carbon atoms; $R_3$ is lower alkyl of from 1 to 4 carbon atoms; Y is —N= or —CH=; and Z is —N= or —CH=, with the proviso that Y and Z cannot be identical, can be made by reacting a compound of the structure:

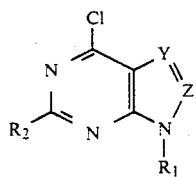

wherein $R_1$ is hydrogen, phenyl or 8-D-ribofuranosyl; $R_2$ is hydrogen or chloride: Y is —N= or —CH=; and Z is —N= or —CH=, with the proviso that Y and Z cannot be identical, with the desired enantiomer of norephridine, as shown below:

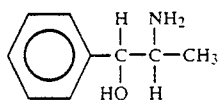

with the recognition that the two carbon atoms designated C exhibit chirality, to form a compound of the structure:

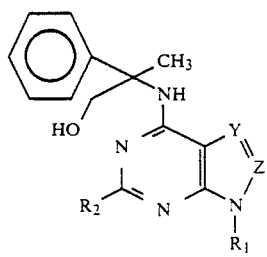

wherein $R_1$ is hydrogen, phenyl or β-D-ribofuranosyl; $R_2$ is hydrogen or chlorine; Y is —N= or —CH=; and Z is —N= or —CH=, with the proviso that Y and Z cannot be identical. The compound shown above can be further reacted with thionyl chloride or a similar agent to produce a compound of the structure:

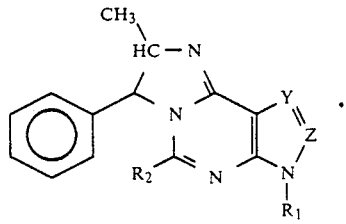

wherein $R_1$ is hydrogen, phenyl or 8-D-ribofuranosyl; and $R_2$ is hydrogen or chloride; Y is —N= or —CH=; and Z is —N= or —CH=, with the proviso that Y and Z cannot be identical.

Furthermore, in a compound of the above structure wherein $R_2$ is chloride, the compound can be further reacted with a selected n-alcohol of from 1 to 4 carbon atoms, such as n-propanol, to form a compound of the structure:

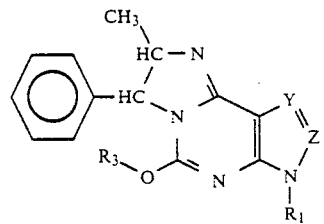

wherein $R_1$ is hydrogen, phenyl or β-D-ribofuranosyl; and $R_3$ is a lower alkyl of from 1 to 4 carbon atoms.

Stereoisomerism is possible with the present compounds and the chemical structure as presented above is considered as encompassing all of the possible stereoisomers and racemic mixtures of such stereoisomers.

As examples of compounds of the present invention are the following:

1. (R)-2,7-dihydro-7-phenyl-2-(phenylmethyl)-5-propoxy-3H-imidazo[1,2-c]pyrazolo[4,3-e]pyrimidine
2. (S)-2,7-dihydro-7-phenyl-2-(phenylmethyl)-5-propoxy-3H-imidazo[1,2-c]pyrazolo[4,3-e]pyrimidine
3. (R)-2,7-dihydro-7-phenyl-2-(phenylmethyl)-3H-imidazo[1,2-c]pyrazolo[4,3-e]pyrimidine
4. (S)-2,7-dihydro-7-phenyl-2-(phenylmethyl)-3H-imidazo[1,2-c]pyrazolo[4,3-e]pyrimidine
5. (S)-7,8-dihydro-3-phenyl-8-(phenylmethyl)-3H-diimidazo[1,2-c:4',5'-e]pyrimidine
6. (R)-7,8-dihydro-3-phenyl-8-(phenylmethyl)-3H-diimidazo[1,2-c:4',5'-e]pyrimidine
7. (2R-trans)-2,7-dihydro-2-methyl-3,7-diphenyl-5-propoxy-3H-Imidazo[1,2-c]pyrazolo[4,3-e]pyrimidine
8. (2S-trans)-2,7-dihydro-2-ethyl-3,7-diphenyl-5-propoxy-3H-Imidazo[1,2-c]pyrazolo[4,3-e]pyrimidine
9. (R)-7,8-dihydro-8-(phenylmethyl)-1H-diimidazo[1,2-c:4',5'-e]pyrimidine
10. (S)-7,8-dihydro-8-(phenylmethyl)-1H-diimidazo[1,2-c:4',5'-e]pyrimidine
11. (R)-7,8-dihydro-3-phenyl-8-(phenylmethyl)-5-propoxy-3H-diimidazo[1,2-c:4',5'-e]pyrimidine
12. (S)-7,8-dihydro-3-phenyl-8-(phenylmethyl)-5-propoxy-3H-diimidazo[1,2-c:4',5'-e]pyrimidine
13. (S)-7,8-dihydro-3-(β-D-ribofuranosyl)-8-(phenylmethyl)-3H-diimidazo[1,2-c:4',5'-e]pyrimidine
14. (R)-7,8-dihydro-3-(β-D-ribofuranosyl)-8-(phenylmethyl)-3H-diimidazo[1,2-c:4',5'-e]pyrimidine
15. (R)-2,7-dihydro-2-(phenylmethyl)-7(β-D-ribofuranosyl)-3H-imidazo[1,2-c]pyrazolo[4,3-e]pyrimidine
16. (S)-2,7-dihydro-2-(phenylmethyl)-7-,(β-D-ribofuranosyl)-3H-iidazo[1,2-c]pyrazolo[4,3-e]pyrimidine
17. (R)-2,7-dihydro-7-(β-D-ribofuranosyl)-2-(phenylmethyl)-5-propoxy-3H-imidazo[1,2-c]pyrazolo[4,3-e]pyrimidine
18. (S)-2,7-dihydro-7-(β-D-ribofuranosyl)-2-(phenylmethyl)-5-propoxy-3H-imidazo[1,2-c]pyrazolo[4,3-e]-pyrimidine.

Therapeutic Utility Of Selective Adenosine Receptor Agents

The table below shows in more detail the therapeutic utility of selective adenosine receptor agents in accordance with the present invention:

| Area | Effect | Receptor Correlate |
| --- | --- | --- |
| Cardiovascular | cardiotonic | A-1 antagonism |
| Cardiovascular | control tachycardia | A-1 agonism |
| Cardiovascular | increase coronary blood flow | A-2 agonism |
| Cardiovascular | vasodilation | A-2 (atypical) agonism |
| Pulmonary | bronchodilation | A-1 antagonism |
| Pulmonary | mediation of autocoid release from mast cells, basophils | novel adenosine receptor interaction on cell surface |
| Pulmonary | stimulate resperation; treat paradoxical ventilatory response (infants) | Ado antagonism |
| Renal | inhibit renin release | A-1 agonism |
| Central nervous system | aid in opiate withdrawal | Ado agonism |
| Central nervous system | analgesic | A-1 agonism |
| Central nervous system | anticonvulsant | A-1 agonism |
| Central nervous system | antidepressant | A-1 agonism |
| Central nervous system | antipsychotic | Ado agonism |
| Central nervous system | anxiolytic | agonism |
| Central nervous system | inhibition of self-mutilation behavior (Lesch-Nyhan syndrome) | Ado agonism |
| Central nervous system | sedative | A-2 agonism |

In the cardiovascular, pulmonary and renal system targets, designed compounds which are identified by receptor binding studies can be evaluated in functional in vivo tests which are directly indicative of the human physiological response. A good description of the pharmacology and functional significance of purine receptors is presented by M. Williams in *Ann. Rev. Pharmacol. Toxicol.*, 27, 31 (1987). In a section entitled "Therapeutic Targeting of Adenosine Receptor Modulators" it is stated that "adenosine agonists may be effective as antihypertensive agents, in the treatment of opiate withdrawal, as modulators of immune competence and renin release, as antipsychotics and as hypnotics. Conversely, antagonists may be useful as central stimulants, inotropics, cardiotonics, antistress agents, antiasthmatics, and in the treatment of respiratory disorders." The smorgasbord of activities displayed by adenosine receptor agents underscores their great potential utility for therapy and the need for central agents.

Adenosine exerts its various biological effects via action on cell-surface receptors. These adenosine receptors are of two types: A-1 and A-2. The A-1 receptors are operationally defined as those receptors at which several N6-substituted adenosine analogs such as R-phenylisopropyladenosine (R-PIA) and cycloadenosine (CHA) are more potent than 2-chloroadinosine and N-5'-ethylcarboxamidoadenosine (NECA). At A-2 receptors the order of potency is instead NECA>2-chloroadenosine>R-PIA>CHA.

As illustrated in the table above, adenosine receptors govern a variety of physiological functions. The two major classes of adenosine receptors have already been defined. These are the A-1 adenosine receptor, which is inhibitory of adenylate cyclase, and the A-2 adenosine receptor, which is stimulatory to adenylate cyclase. The A-1 receptor has a higher affinity for adenosine and adenosine analogs than the A-2 receptor. The physiological effects of adenosine and adenosine analogs are complicated by the fact that nonselective adenosine receptor agents first bind the rather ubiquitous low-affinity A-2 receptors, then as the dose is increased, the high-affinity A-2 receptors are bound, and finally, at much higher doses, the very high-affinity A-1 adenosine receptors are bound. (See J. W. Daly, et al., Subclasses of Adenosine Receptors in the Central Nervous System:Interaction with Caffeine and Related Methylxanthines. *Cellular and Molecular Neurobiology*, 3(1), 69–80 (1983).

In general, the physiological effects of adenosine are mediated by either the stimulation or the inhibition of adenylate cyclase. Activation of adenylate cyclase increases the intracellular concentration of cyclic AMP, which, in general, is recognized as an intracellular second messenger. The effects of adenosine analogs can therefore be measured by either the ability to increase or the ability to antagonize the increase in the cyclic AMP in cultured cell lines. Two important cell lines in this regard are VA 13 (WI-38 VA 13 2RA), SV-40 transformed WI 38 human fetal lung fibroblasts, which are known to carry the A-2 subtype of adenosine receptor, and fat cells, which are known to carry the A-1 subtype of adenosine receptor. (See R. F. Bruns, Adenosine Antagonism by Purines, Pteridines and Benzopteridines in Human Fibroblasts, *Biochemical Pharmacology*, 30, 325–33, (1981).

It is well known from in vitro studies that the carboxylic acid congener of 8-phenyl-1,3-dipropyl-xanthine (XCC) is adenosine receptor non-selective, with a Ki at the A-1 receptors in brain membranes of 58±3nM and a Ki at the A-2 receptors of the brain slice assay of 34±13nM. The amino congener of 8-phenyl-1,3-dipropyl-xanthine (XAC), on the other hand, has a 40-fold higher affinity for A-1 adenosine receptors, with a Ki of 1.2±0.5nM, as compared with a Ki at the A-2 receptors of the brain slice assay of 49±17nM. In addition, XAC is much more potent in antagonizing the effects of adenosine analogs on heart rate than on blood pressure. Since it is generally known that the adenosine analog-induced effects on the heart seem to be mediated via A-1 receptors and those on blood pressure via A-2 receptors, the selectivity of XAC under in vivo conditions suggests that adenosine receptor activity in vitro correlates with adenosine receptor activity in vivo and that specific physiological effects can be distinguished as a result of this selectivity. (See B. B. Fredholm, K. A. Jacobsen, B. Jonzon, K. L. Kirk, Y. O. Li, and J. W. Daly, Evidence That a Novel 8-Phenyl-Substituted Xanthine Derivative is a Cardioselective Adenosine Receptor Antagonist In Vivo, *Journal of Cardiovascular Pharmacology*, 9, 396–400, (1987) and also K. A. Jacobsen, K. L. Kirk, J. W. Daly, B. Jonzon, Y. O. Li, and B. B. Fredholm, Novel 8-Phenyl-Substituted Xanthine Derivative Is Selective Antagonist At Adenosine Receptors In Vivo, *Acta Physiol. Scand.*, 341–42, (1985).

It is also known that adenosine produces a marked decrease in blood pressure. This blood pressure reduction is probably dependent upon an A-2 receptor-mediated decrease in peripheral resistance. Adenosine analogs are also able to decrease heart rate. This effect is probably mediated via adenosine receptors of the A-1 subtype.

Thus, it is readily apparent that the pharmacological administration of the adenosine receptor selective adenosine analogs disclosed herein will result in selective binding to either the A-2 or the A-1 receptor, which will, in turn, selectively result in either a decrease in blood pressure or a decrease in heart rate, for example, thereby decoupling these physiological effects in vivo. The selection of such adenosine receptor selective agents can be determined by the methods described in further detail below.

Test For Affinity For Brain Adenosine A-2 Receptors

The test described below was used to determine the potency of test compounds to compete with the ligand [3H]5'-N-ethylcarboxamidoaeenosine (NECA) for the adenosine A-2 prepared from animal brain membranes. (See also R. R. Bruns, G. H. Lu, and T. A. Pugsley, Characterization of the A-2 Adenosine Receptor Labeled by [3H]NECA in Rat Striatal Membranes, *Mol. Pharmacol.*, 29, 331–346 (1986). Young male rats (C-D strain), obtained from Charles River, are killed by decapitation and the brain was removed. Membranes for ligand binding are isolated from rat brain striatum. The tissue is homogenized in 20 vol. icecold 50 mM Tris-HCl buffer (pH 7.7) using a polytron (setting for 6 to 20 seconds). The homogenate is centrifuged at $50,000 \times g$ for 10 minutes at 4° C. The pellet is again homogenized in a polytron in 20 vol. of buffer, and centrifuged as before. The pellet is finally resuspended in 40 vol. of 50mM Tris-HCl (pH 7.7) per gram of original wet weight of tissue.

Incubation tubes, in triplicate, receive 100 µl of [3H]NECA (94 nM in the assay), 100 µl of 1 µM cyclohexyladenosine (CHA), 100 µl of 100 mM $MgCl_2$, 100 µl of 1 IU/ml adenosine deaminase, 100 µl of test compounds at various concentrations over the range of $10^{-10}$ M to $10^{-4}$ M diluted with assay buffer (50 mM Tris-HCl, pH 7.7) and 0.2 µl of membrane suspension (5 mg wet weight), in a final volume of 1 ml of 50 mM Tris-HCl, pH 7.7. Incubations are carried out at 25° C. for 60 minutes. Each tube is filtered through GF/B glass fiber filters using a vacuum. The filters are rinsed two times with 5 ml of the ice-cold buffer. The membranes on the filters are transferred to scintillation vials to which 8 ml of Omnifluor with 5% Protosol is added. The filters are counted by liquid scintillation spectrometry.

Specific binding of [3H]NECA is measured as the excess over blanks run in the presence of 100 µM 2-chloroadenosine. Total membrane-bound radioactivity is about 2.5% of that added to the test tubes. Since this condition limits total binding to less than 10% of the radioactivity, the concentration of free ligand does not change appreciably during the binding assay. Specific binding to membranes is about 50% of the total bound. Protein content of the membrane suspension is determined by the method of O. H. Lowry, N. J. Rosebrough, A. L. Farr and R. J. Randall, Protein Measurements With Folin Phenol Reagent, *J. Biol. Chem.*, 193, 265–275 (1951).

Displacement of [3H]NECA binding of 15% or more by a test compound is indicative of affinity for the adenosine A-2 site. The molar concentration of a compound which causes 50% inhibition of the binding of ligand is the $IC_{50}$. A value in the range of 100–1000 nM would indicate a highly potent compound.

Test For Affinity For Brain Adenosine A-1 Receptor Binding Sites

The test described below is used to determine the potency of test compounds to compete with the ligand [3H]cycloadenosine for the Adenosine A-1 receptor prepared from rat brain membranes. Male Sprague-Dawley rats are sacrificed by decapitation and the membranes are isolated from whole animal brains. (See R. Goodman, M. Cooper, M. Gavish, and S. Synder, Guanine Nucleotide and Cation Regulation of the Binding of [3H]Diethylphenylxanthine to Adenosine A-1 Receptors in Brain Membrane, *Molecular Pharmacology*, 21, 329–335 (1982).

Membranes are homogenized (using polytron setting 7 for 10 seconds) in 25 volumes of ice-cold 50 mM Tris-HCl buffer, pH 7.7. The homogenate is centrifuged at 19,000 rpm for 10 minutes at 4° C. The pellet is washed by resuspending in 25 volumes of buffer with 2 IU of adenosine deaminase per ml and incubated 30 minutes at 37° C. The homogenate is centrifuged again. The final pellet is resuspended in 25 volumes of ice-cold buffer.

The incubation tubes, in triplicate, receive 100 µl of [3H]cyclohexyladenosine, 0.8 nM in the assay, 200 µl of test compounds at various concentrations over the range of $10^{-10}$ M to $10^{-6}$ M diluted with 50 nM Tris-HCl buffer (pH 7.7), 0.2 ml of membrane suspension (8 mg wet weight) and in a final volume of 2 ml with Tris buffer. Incubations are carried out at 25° C. for 2 hours and each one is terminated within 10 seconds by filtration through a GF/B glass fiber filter using a vacuum. The membranes on the filters are transferred to scintillation vials. The filters are counted by liquid scintillation spectrometry in 8 ml of Omnifluor containing 5% Protosol.

Specific binding of [3H]cycloadenosine is measured as the excess over blanks taken in the presence of $10^{-5}$ M 2-chloroadenosine. Total membrane-bound radioactivity is about 5% of that added to the test tubes. Specific binding to membranes is about 90% of the total bound. Protein content of the membrane suspension is determined by the method of Lowry, et al. Id., 265.

Displacement of [3H]cyclohexyladenosine binding of 15% or more by a test compound is indicative of affinity for the adenosine binding site.

Adenosine Receptor Binding Affinity Values Obtained Using The Above Described Test Procedures The following is a table showing the adenosine receptor binding affinities for the compounds identified previously (refer to compound examples above for cross reference to compound names) within the scope of the present invention:

| Compound | A-1 Receptor Ki | A-2 Receptor Ki | A-2 Ki/A-1 Ki |
|---|---|---|---|
| 1. | $1.24 \times 10^{-6}$ | $>6.99 \times 10^{-6}$ | — |
| 2. | $2.68 \times 10^{-6}$ | $5.08 \times 10^{-7}$ | 0.18 |
| 3. | $1.90 \times 10^{-6}$ | $2.50 \times 10^{-5}$ | 13.20 |
| 4. | $1.00 \times 10^{-5}$ | $>1.99 \times 10^{-4}$ | — |
| 5. | $4.46 \times 10^{-5}$ | $>1.99 \times 10^{-4}$ | — |
| 6. | $8.40 \times 10^{-6}$ | $1.00 \times 10^{-4}$ | 16.40 |
| 7. | $1.21 \times 10^{-5}$ | $1.42 \times 10^{-5}$ | 1.17 |
| 8. | $2.64 \times 10^{-5}$ | $2.85 \times 10^{-5}$ | 1.07 |
| 9. | $1.99 \times 10^{-4}$ | $>1.99 \times 10^{-4}$ | — |
| 10. | $1.99 \times 10^{-4}$ | $>1.99 \times 10^{-4}$ | — |
| 11. | N/A | N/A | — |
| 12. | $9.00 \times 10^{-6}$ | $1.60 \times 10^{-6}$ | 0.18 |
| 13. | $4.50 \times 10^{-6}$ | $1.06 \times 10^{-5}$ | 1.70 |
| 14. | $6.50 \times 10^{-5}$ | $4.68 \times 10^{-5}$ | 5.50 |

The nucleotide guanosine triphosphate (GTP) has been shown to differentially affect the binding of agonists and antagonists to a variety of neurotransmitter receptors. In general, guanine nucleotides lower the affinity of agonists for receptors without a concomitant decrease in antagonist affinity. Accordingly, GTP has been shown to decrease the potency of agonists but not antagonists as inhibitors of the binding of the adenosine antagonist [3H]3-diethyl-8-phenylxanthine. In general, GTP greatly reduces the potency of purine agonists, but not antagonists, as inhibitors of [3H]phenylisopropyl adenosine binding and is, therefore, an effective agent for distinguishing between agonists and antagonists. (See L. P. Davies, S. C. Chow, J. H. Skerritt, D. J. Brown and G. A. R. Johnston, Pyrazolo[3,4-d]Pyrimidines as Adenosine Antagonists, *Life Sciences*, 34, 2117-28, (1984). It is understood, in general, that adenosine analogs act as agonists if β-D-ribofuranosyl is present in the molecule at the $R_1$ position and as an antagonist if $R_1$ is hydrogen or phenyl.

Pharmaceutical Preparations of the Adenosine Receptor Selective Adenosine Agents The exact amount of the compound or compounds to be employed, i.e., the amount of the subject compound or compounds sufficient to provide the desired effect, depends on various factors such as the compound employed; type of administration; the size, age and species of animal; the route, time and frequency of administration; and, the physiological effect desired. In particular cases, the amount to be administered can be ascertained by conventional range finding techniques.

The compounds are preferably administered in the form of a composition comprising the compound in admixture with a pharmaceutically acceptable carrier, i.e., a carrier which is chemically inert to the active compound and which has no detrimental side effects or toxicity under the conditions of use. Such compositions can contain from about 0.1 µg or less to 500 mg of the active compound per ml of carrier to about 99% by weight of the active compound in combination with a pharmaceutically-acceptable carrier.

The compositions can be in solid forms, such as tablets, capsules, granulations, feed mixes, feed supplements and concentrates, powders, granules or the like; as well as liquid forms such as sterile injectable suspensions, orally administered suspensions or solutions. The pharmaceutically acceptable carriers can include excipients such as surface active dispersing agents, suspending agents, tableting binders, lubricants, flavors and colorants. Suitable excipients are disclosed, for example, in texts such as *Remington's Pharmaceutical Manufacturing*, 13 Ed., Mack Publishing Co., Easton, Pa. (1965).

The following examples are presented to illustrate the present invention but they should not be construed as limiting in any way.

EXAMPLE 1

First, 2.81 g of 1-phenyl-4,6-dichloropyrazolo[3,4-d]pyrimidine was suspended in 60 ml ethanol. Then 3.2 g of R-(+)-2-amino-3-phenyl-1-propanol was added with stirring. After 48 hours the solvent was removed under vacuum and the oil was flash chromatographed (2-5-7% MeOH/CHCl$_3$) to yield 3.80 g of product (R)-β-[(1-phenyl-6-chloro-1H-pyrazolo[3,4-d]pyrimidin-4-yl)amino]benzenepropanol (95%).

Next, 1.234 g of (R)-β-[(1-phenyl-6-chloro-1H-pyrazolo[3,4-d]pyrmiidin-4-yl)amino]benzenepropanol was dissolved in 50 ml CHCl$_3$ and 1.69 ml SOCl$_2$ was added with stirring. After 6 hours it was placed in a freezer at $-28°$ C. overnight. It was then filtered and the white precipitate was rinsed with 50 ml cold CHCl$_3$. The white solid was collected and dried in a vacuum oven at 70° C. for 24 hours to yield 650 mg of product (R)-2,7-dihydro-7-phenyl-2-(phenylmethyl)-5-chloro-3H-imidazo[1,2-c]pyrazolo[4,5-e]pyrimidine.

50 mg sodium was reacted in 20 ml n-propanol. Next, 650 mg of (R)-2,7-dihydro-7-phenyl-2-(phenylmethyl)-5-chloro-3H-imidazo[1,2-c]pyrazolo[4,5-e]pyrimidine was added with stirring under nitrogen. After 1.5 hours at room temperature, the cloudy white reaction was poured into 100 ml saturated NaCl and extracted with 200 ml CHCl$_3$. The organic layer was dried over MgSO$_4$, filtered and concentrated to yield an oil which was purified by radial chromatography (10-20-30% isopropyl alcohol/hexane, 4 mm plate) to yield 200 mg of product. Thin layer chromatography in two separate systems showed a clean product. Recrystallization of the above product yielded 132 mg of (R)-2,7-dihydro-7-phenyl-2-(phenylmethyl)-5-propoxy-3H-imidazo[1,2-c]pyrazolo[4,5-e]-pyrimidine, a white solid (m.p. 45°–48° C.).

EXAMPLE 2

First, 5.0 g of 6-chloropurineriboside was suspended in 100 ml dry CH$_2$Cl$_2$ followed by addition of 8.02 ml triethylamine. The reaction was cooled to 0° C. followed by addition of 6.68 ml benzoyl chloride dropwise. After addition of chloride the reaction was allowed to warm to room temperature and stir for 24 hours. The solvent was removed under vacuum and the residue dissolved in 500 ml ethyl alcohol. The organic layer was rinsed with 300 ml water, 300 ml saturated NaHCO$_3$, 3 times, 300 ml saturated NaCl, dried over MgSO$_4$, filtered and concentrated to yield a brown oil. This was purified by flash chromatography (10-30-60% ethyl alcohol/hexane) to yield 10.3 g 6-chloro-9-β-D-ribofuranosyl-2,3,5-tribenzoate-9H-purine.

Next, 4.0 g of 6-chloro-9-β-D-ribofuranosyl-2,3,5-tribenzoate-9H-purine was combined with 1.01 g of (R)-(+)-2-amino-3-phenyl-1-propanol, 0.92 ml Et$_3$N and 100 ml absolute ethanol and heated to reflux for 4 hours. The solvent was then removed under vacuum and the residue purified by flash chromatography (5-10-20% methanol/CHCl$_3$) to yield about 3.5 g of product as impure material. This was again chromatographed (5–10% methanol/CHCl$_3$) to yield 3.35 g of product. This was again chromatographed to yield 1.78 g of clean product, (R)-β-[(9-β-D-ribofuranosyl-2,3,5-tribenzoate-9H-purine-6-yl)amino]benzenepropanol and 1.26 g of impure material.

Next, 1.78 g of the above clean product (R)-β-[(9-β-D-ribofuranosyl-2,3,5-tribenzoate-9-H-purine-6-yl)amino]benzenepropanol was dissolved in 60 ml dry CHCl$_3$ and treated with 1.3 ml SOCl$_2$. It was then heated to reflux for 4 hours and then cooled to room temperature overnight. The solvent was then removed under vacuum to yield 1.94 g of product. This was purified by flash chromatography (5% MeOH/CHCl$_3$) to yield 300 mg of a first product and 1,200 mg of a second product. The second product was radial chromatographed (2-4-6% MeOH/CHCl$_3$, 2mm plate) two times to yield 1.10 g of a foam product, R-7,8-dihydro-3-(β-D-ribofuranosyl-2,3,5-tribenzoate)-8-(phenylmethyl)-3H-diimidazo[1,2-c:4',5'-e]pyrimidine.

Subsequently, 580 mg of the foam product R-7,8-dihydro-3-(β-D-ribofuranosyl-2,3,5-tribenzoate)-8-(phenylmethyl)-3H-diimidazo[1,2-c:4',5'-e]pyrimidine was dissolved in 20 ml methanol and treated with a catalytic amount to NaOMe. After 2 hours, thin layer chromatography indicated completion of reaction. The solvent was removed and the residue was purified by radial chromatography (20%–50% MeOH/CHCl₃, 1 mm plate) to yield about 300 mg of a foam. This was recrystallized from about 30% isopropyl alcohol/hexane to yield after drying under vacuum at 39° C. for 144 hours 168 mg of R-7,8-dihydro-3-(β-D-ribofuranosyl)-8-(phenylmethyl)-3H-diimidazo[1,2-c:4',5'-e]pyrimidin (m.p. 140°–143°C.).

EXAMPLE 3

First, 1.13 g of the starting material 4-chloro-1-phenylpyrazolo[3,4-d]pyrimidine was combined with 0.67 ml Et₃N, 0.74 g of (R)-(+)-2-amino-3-phenyl-1-propanol in 60 ml absolute ethanol and heated in a steam bath for four hours. The solvent was then removed under vacuum and the residue was purified by flash chromatography (10–20% isopropyl alcohol/hexane) to yield 1.24 g of (R)-β-[1-phenyl-1H-pyrazolo[3,4-d]pyrimidin-4-yl)amino]benzenepropanol (74% yield).

Next, 1.24 g of (R)-β-[1-phenyl-1H-pyrazolo[3,4-d]pyrimidin-4-yl)amino]benzenepropanol was dissolved in 60 ml dry CHCl₃, 1.82 ml SOCl₂ was added and the reaction was heated to reflux for 4 hours. After cooling, the solvent was removed and the precipitate taken up in butanone. The white suspension was filtered yielding a white powder, which was recrystallized from about 5% MeOH/butanone to yield after oven drying under vacuum at 85° C. for 4 hours, 229.4 mg of long, flat, clear crystals, (R)-2,7-dihydro-7-phenyl-2-(phenylmethyl)-3H-imidazo[1,2-c]pyrazolo[4,3-e]pyrimidine (m.p. 270° C.).

EXAMPLE 4

First, 2.0 g of 6-chloro-9-phenylpurine was combined with 1.38 g (S)-(−)-2-amino-3-phenyl-1-propanol, 1.27 ml Et₃N, 50 ml absolute ethanol and heated to reflux for 5 hours. The solvent was then removed under vacuum and the residue purified by flash chromatography (2.5–5% MeOH/CHCl₃) to yield 2.27 g of product (76% yield). This was recrystallized from isopropyl alcohol/hexane at about 10% to yield after drying under vacuum at 90° C. for 3 days 0.87 g of a white solid (R)-β-[(9-phenyl-9H-purin-6-yl)amino]benzenepropanol (m.p. 130°–132° C.).

Next, 1.13 g of (R)-β-[(9-phenyl-9H-purin-6-yl)amino]benzenepropanol was dissolved in 50 ml CH₂Cl₂ with 1.7 ml SOCl₂ and heated to reflux for 6 hours. The solvent was then removed under vacuum, the residue taken up in butanone and filtered. The white precipitate was recrystallized from about 5% MeOH/butanone to yield after drying under vacuum at 39° C. for 2 days 530 mg of (S)-7,8-dihydro-3-phenyl-8-(phenylmethyl)-5-propoxy-3H-diimidazo[1,2-c:4',5'-e]pyrimidine (m.p. 270° C.).

EXAMPLE 5

First, 5.0 g of 6-chloropurine riboside was suspended in 100 ml dry CH₂Cl₂ followed by addition of 8.02 ml triethylamine. The reaction was cooled to 0° C. followed by addition of 6.68 ml benzoyl chloride dropwise. After addition of chloride the reaction was allowed to warm to room temperature and stirred for 24 hours. The solvent was removed under vacuum and the residue dissolved in 500 ml ethyl alcohol. The organic layer was rinsed with 300 ml water, 300 ml saturated NaHCO₃, 3 times, 300 ml saturated NaCl, dried over MgSO₄, filtered and concentrated to yield a brown oil. This was purified by flash chromatography (10-30-60% ethyl alcohol/hexane) to yield 10.3 g 6-chloro-9-β-D-ribofuranosyl-2,3,5-tribenzoate-9H-purine.

Next, 4.0 g of 6-chloro-9-β-D-ribofuranosyl-2,3,5-tribenzoate-9H-purine was combined with 1.01 g of (S)-(−)-2-amino-3-phenyl-1-propanol and 0.92 ml of Et₃N in absolute ethanol (100 ml) and heated to reflux for 4 hours. The solvent was then removed under vacuum and the residue purified by flash chromatography (5% MeOH/CHCl₃) to yield 2.36 g of (S)-β-[(9-β-D-ribofuranosyl-2,3,5-tribenzoate-9H-purine-6-yl)amino]benzenepropanol and 1.73 g of impure material.

Next, 2.36 g of (S)-β-[(9-β-D-ribofuranosyl-2,3,5-tribenzoate-9-H-purine-6-yl)amino]benzenepropanol was dissolved in 80 ml dry CH₂Cl₂ and treated with 1.7 ml SOCl₂. The reaction was heated to reflux for 4 hours, cooled to room temperature, stirred overnight and the solvent removed under vacuum. The residue was purified by flash chromatography (5% MeOH/CHCl₃) to yield 1.77 g of S-7,8-dihydro-3-(β-D-ribofuranosyl-2,3,5-tribenzoate)-8-(phenylmethyl)-3H-diimidazo[1,2-c:4',5'-e]pyrimidine (77% yield).

The 1.77 g of S-7,8-dihydro-3-(β-D-ribofuranosyl-2,3,5-tribenzoate)-8-(phenylmethyl)-3H-diimidazol[1,2-c:4',5'-e]-pyrimidine was dissolved in 60 ml methanol and treated with a catalytic amount of NaOMe. After 24 hours, the solvent was removed under vacuum and the residue purified by flash chromatography (10-20-50% MeOH/CHCl₃, 2 mm plate) to yield 700 mg of product. This was triturated with ether/hexane (about 5%), dried under vacuum at 39° C. for 6 days to yield 470 mg of S-7,8-dihydro-3-(β-D-ribofuranosyl)-8-(phenylmethyl)-3H-diimidazo[1,2-c:4',5'-e]pyrimidine.

EXAMPLE 6

2.5 g of the starting material 1-phenyl-4,6-dichloropyrazolo[3,4-d]pyrimidine was suspended in 60 ml of ethanol. Next, 4.28 g of (S)-(−)-2-amino-3-phenyl-1-propanol was added and the reaction was allowed to stir for 24 hours. The solvent was then removed under vacuum and the crude oil was purified by flash chromatography (10-15-20% isopropyl alcohol/hexane) to yield 3.5 g of (S)-β-[(1-phenyl-6-chloro-1H-pyrazolo[3,4-d]pyrimidin-4-yl)amino]benzenepropanol (97%).

1.037 g of the above product (S)-β-[(1-phenyl-6-chloro-1H-pyrazolo[3,4-d]pyrimidin-4-yl)amino]benzenepropanol was then dissolved in 25 ml CHCl₃. Next, 1.38 ml thionyl chloride was added and the reaction was allowed to stir overnight. It was then placed in a freezer at −28° C. After 5 hours the precipitate was filtered and collected washing with cold CHCl₃. The white solid was dried in a vacuum oven at 70° C. for 24 hours to yield 550 mg of (S)-2,7-dihydro-7-phenyl-2-(phenylmethyl)-5-chloro-3H-imidazo[1,2-c]pyrazolo[4,3-e]pyrimidine (56%).

Then, 20 mg sodium was reacted in 3 ml n-propanol. The solution was cooled with an ice bath and 209 mg of the above product (S)-2,7-dihydro-7-phenyl-2-(phenylmethyl)-5-chloro-3H-imidazo[1,2-c]pyrazolo[4,3-e]pyrimidine was added with stirring. After 1 hour the reaction was poured into 100 ml saturated NaCl solution and extracted with 200 ml CHCl₃. The organic layer was dried over MgSO₄, filtered and concentrated to yield an oil which was purified by radial chromatography (5–10% MeOH/ CHCl₃, 2 mm plate) to yield 168 mg of (S)-2,7-dihydro-7-phenyl-2-(phenylmethyl)-5-propoxy-3H-imidazo[1,2-c]pyrazolo[4,3-e]pyrimidine (75%).

EXAMPLE 7

First, 2 g of the starting material 1-phenyl-4,6-dichloropyrazolo[3,4-d]pyrimidine was suspended in 50 ml ethanol followed by the addition of 5.6 g of 1S,2R-norephedrine. After stirring for 24 hours the solvent was removed under vacuum and the crude material was purified by flash chromatography (10% isopropyl alcohol/hexane) to yield 1.90 g of [R-(S*,R*)]-α-[1-[(1-phenyl-6-chloro-1H-pyrazolo[3,4-d]pyrimidin-4-yl)amino]ethyl]benzenemethanol.

Next, 1.9 g of the above product [R-(S*,R*)]-α-[1-[(1-phenyl-6-chloro-1H-pyrazolo[3,4-d]pyrimidin-4-yl)amino]ethyl]benzenemethanol was combined with 2.2 ml SOCl$_2$ in 150 ml CH$_3$CN with stirring. After 20 hours the solvent was removed under vacuum and the brown residue taken up in 250 ml CHCl$_3$. The organic was rinsed with 200 ml H$_2$O, 200 ml saturated NaCl, dried over MgSO$_4$, filtered and concentrated to yield a brown oil which was purified by flash chromatography (50% ethanol/hexane) to yield 850 mg of a clear viscous oil (2R-trans)-2,7-dihydro-2-methyl-3,7-diphenyl-5-chloro-3H-imidazo[1,2-c]pyrazolo[4,3-e]pyrimidine.

51 mg sodium was dissolved in 5 ml n-propanol. 670 mg of the above product (2R-trans)-2,7-dihydro-2-methyl-3,7-diphenyl-5-chloro-3H-imidazo[1,2-c]pyrazolo[4,3-e]pyrimidine dissolved in 15 ml n-propanol was added to the propoxide solution with stirring. After 1 hour the reaction was poured into 200 ml saturated NaCl and the extracts were dried over MgSO$_4$, filtered and concentrated to yield an oil which was purified by radial chromatography (30-50-70-90% ethanol/hexane, 2 mm plate) to yield 600 mg of (2R-trans)-2,7-dihydro-2-methyl-3,7-diphenyl-5-propoxy-3H-imidazo[1,2-c]pyrazolo[4,3-e]pyrimidine.

EXAMPLE 8

First, 2.0 g of 6-chloro-9-phenylpurine was combined with 1.38 g of (R)-(+)-2-amino-3-phenyl-1-propanol, 1.27 ml Et$_3$N, 50 ml absolute ethanol and heated to reflux for 5 hours. The solvent was then removed and the residue was purified by flash chromatography (5% MeOH/CHCl$_3$), followed by a second purification (2.5-5% MeOH/CHCl$_3$), to yield 2.66 g of a white foam (88% yield). This was recrystallized from about 10% isopropyl alcohol/hexane and dried under vacuum at 90° C. for 4 days to yield 1.28 g of a white solid, (R)-β-[(9-phenyl-9-H-purin-6-yl)amino]benzenepropanol (m.p. 130°-132° C.).

Next, 1.0 g of the above product (R)-β-[(9-phenyl-9-H-purin-6-yl)amino]benzenepropanol was dissolved in 50 ml CH$_2$Cl$_2$ with 1.5 ml SOCl$_2$ and heated to reflux for 6 hours. The solvent was removed under vacuum, the residue taken up in butanone and filtered. The white precipitate was recrystallized from about 5% methanol/butanone to yield after drying under vacuum for 3 days 430 mg of (R)-7,8-dihydro-3-phenyl-8-(phenylmethyl)-3H-diimidazo[1,2-c:4'5'-e]pyrimidine.

EXAMPLE 9

First, 2.5 g of 6-chloropurine was dissolved in 60 ml absolute ethanol followed by addition of 2.25 ml Et$_3$N and 2.45 g of R-(+)-2-amino-3-phenyl-1-propanol with stirring. The reaction was removed under vacuum and the residue was purified by flash chromatography (10-15% MeOH/ CHCl$_3$) to yield 3.35 g of product. This was recrystallized by about 40% isopropyl alcohol/hexane to yield 2.23 g of R-β-[(1H-purin-6-yl)amino]benzenepropanol after drying under vacuum at 80° C. for 48 hours.

This was followed by suspension of 1.5 g of the above product R-β-[(1H-purin-6-yl)amino]benzenepropanol in 60 ml dry CH$_2$Cl$_2$, followed by addition of 2.85 ml SOCl$_2$. The reaction was heated to reflux for 4 hours and then allowed to cool to room temperature overnight. The solvent was removed under vacuum and the residue then taken up in 100 ml butanone. This was filtered to yield 1670 mg of a yellow solid. This was recrystallized from 10% MeOH/butanone to yield after oven drying under vacuum at 85° C. 690 mg of product. The free base was prepared by treatment with NaHCO$_3$ and the residue purified by radial chromatography (10-20% MeOH/CHCl$_3$, 2mm plate) to yield after drying under high vacuum at 39° C. for 6 days 97.0 mg of (R)-7,8-dihydro-8-(phenylmethyl)-1H-diimidazo[1,2-c:4'5'-e]pyrimidine (m.p. 140° C.).

EXAMPLE 10

First, 1 g of the starting material 4-chloro-1-phenylpyrazolo[3,4-d]pyrimidine was combined with 651 mg of (S)-(−)-2-amino-3-phenyl-1-propanol and 0.6 ml Et$_3$N in 60 ml absolute ethanol and heated to reflux for 5 hours. The solvent was then removed under vacuum and the residue purified by flash chromatography (10-15-20% isopropyl alcohol/ hexane) to yield a white solid which was recrystallized from about 20% isopropyl alcohol/hexane to yield, after oven drying under vacuum, 1.06 g of (S)-β-[(1-phenyl-1H-pyrazolo[3,4-d]pyrimidin-4-yl)amino]benzenepropanol (m.p. 114°-117° C.).

Next, 300 mg of the above product (S)-β-[(1-phenyl-1H-pyrazolo[3,4-d]pyrimidin-4-yl)amino]benzenepropanol was dissolved in 15 ml CH$_2$Cl$_2$ followed by addition of 0.44 ml SOCl$_2$. The reaction was heated to reflux for 3.5 hours. The solvent was then removed under a stream of nitrogen. The white solid was recrystallized from about 30% isopropyl alcohol/hexane followed by a second recrystallization from about 5% MeOH/butanone to yield 45 mg of (S)-2,7-dihydro-7-phenyl-2-(phenylmethyl)-3H-imidazo[1,2-c]pyrazolo[4,3-e]pyrimidine after drying under vacuum at 39° C. for 5 days (m.p. 255° C.).

EXAMPLE 11

Initially, 2.5 g of 6-chloropurine was suspended in 60 ml ethanol. Next, 2.45 g of (S)-(−)-2-amino-3-phenyl-1-propanol and 2.25 ml Et$_3$N were added and the reaction was allowed to stir for 16 hours at room temperature. Thin layer chromatography indicated no change. It was then heated to reflux for 20 hours. The solvent was then removed under vacuum and the residue purified by flash chromatography (10% MeOH/CHCl$_3$) to yield about 3 g of product. This was recrystallized 2 times with about 40% isopropyl alcohol/hexane to yield after oven drying under vacuum at 80° C. for 72 hours, 2.13 g of a white solid S-β-[(1H-purin-6-yl)amino]benzenepropanol (m.p. 207°-209° C.).

Subsequently, 300 mg of the above product S-β-[(1H-purin-6-yl)amino]benzenepropanol was resuspended in 20 ml CH$_2$Cl$_2$. Then, 0.57 ml SOCl$_2$ was added and the reaction was heated to reflux for 4 hours. The solvent was then removed under vacuum and the white solid taken up in butanone. The suspension was filtered and the white precipitate recrystallized from 5% MeOH/-butanone to yield 116.9 mg of slightly yellow crystals. This was dried under vacuum at 80° C. for 24 hours to yield 88 mg of (S)-7,8-dihydro-8-(phenylmethyl)-1H-diimidazo[1,2-c:4′5′-e]pyrimidine (m.p. 268°–170° C.).

EXAMPLE 12

First, 1.5 g of starting material 1-phenyl-4,6-dichloropyrazolo[3,4-d]pyrimidine was suspended in 40 ml of ethanol. Then, 2.6 g 1R,2S-(−)-norephedrine was added and the reaction was allowed to stir for 48 hours. The solvent was removed and the oil flash chromatographed (50-70% Et₂O/hexane) to yield 2.1 g of [S-(R*,S*)]-α-[1-[(1-phenyl-6-chloro-1H-pyrazolo[3,4-d]pyrimidin-4-yl)amino]ethyl]benzenemethanol.

Next, 700 mg of the above product [S-(R*,S*)]-α-[1-[(1-phenyl-6-chloro-1H-pyrazolo[3,4-d]pyrimidin-4-yl)amino]ethyl]benzenemethanol was dissolved in 50 ml CH₃CN, followed by adding 0.26 ml SOCl₂ with stirring. The reaction was allowed to stir for 24 hours. The solvent was then removed and the residue flash chromatographed (2-4-8-10% MeOH/CHCl₃) to yield 840 mg of a mixture of product and starting material. This was again purified by radial chromatography (20-30-50% ethanol/hexane, 4 mm plate) to yield 210 mg of (2S-trans)-2,7-dihydro-2-methyl-3,7-diphenyl-S-chloro-3H-imidazo[1,2-c]pyrazolo[4,3-e]pyrimidine.

Subsequently, about 16 mg of sodium was dissolved in 1 ml n-propanol, followed by adding 210 mg of the above product (2S-trans)-2,7-dihydro-2-methyl-3,7-diphenyl-S-chloro-3H-imidazo[1,2-c]pyrazolo[4,3-e]pyrimidine in 4 ml n-propanol with stirring producing the white precipitate (NaCl). After 3 hours the reaction was poured into 100 ml saturated NaCl and extracted with CHCl₃ (2 times, 100 ml). The combined organic extracts were reduced under vacuum to yield an oil which was purified by radial chromatography (2% MeOH/CHCl₃, 2mm plate) to yield 217 mg of a white foam. This was dried for 8 days over P₂O₅ under vacuum to provide about 180 mg of (2S-trans)-2,7-dihydro-2-methyl-3,7-diphenyl-5-propoxy-3H-imidazo[1,2-c]pyrazolo[4,3-e]pyrimidine.

EXAMPLE 13

100 g of violuric acid was added to 1 liter of water with vigorous overhead stirring and heated to 70° C. 200 g sodium hydrosulfite was added in portions over 15 minutes. After 2.5 hours the reaction was filtered and the precipitate rinsed with water. The solid was dried under vacuum at 98° C. for 3 hours to yield 75 g of 5-amino-2,4,6-trihydroxypyrimidine.

75 g of 5-amino-2,4,6-trihydroxypyrimidine was dissolved in 1.5 to 5% sodium hydroxide with vigorous overhead stirring producing a violet solution. The reaction was heated to 60° C. and 63 ml phenyl isothiocyanate was added dropwise over 1.5 hours. The reaction turned pale yellow. The reaction was stirred an additional 2 hours at 60° C., cooled and acidified with glacial acetic acid producing a light yellow precipitate. This was filtered to yield about 75 g of N-(2,4,6-trihydroxy-5-pyrimidyl)-N′-phenylthiourea.

About 75 g of N-(2,4,6-trihydroxy-5-pyrimidyl)-N′-phenylthiourea was combined with 600 ml concentrated hydrochloric acid and heated to reflux for 5 hours (considerable foaming occurred). It was then diluted with 2 liters of water and immediately filtered and washed with water. This was dried under vacuum at 80° C. for 2 days to yield 50.08 g of product (34% yield from violuric acid). A small sample was triturated with hot glacial acetic acid to yield intermediate 2,6-dihydroxy-9-phenyl-8-purinethiol.

10 g of 2,6-dihydroxy-9-phenyl-8-purinethiol was dissolved in about 100 ml 1N sodium hydroxide followed by addition of about 30 g Raney nickel. Slight foaming occurred. The reaction was slowly heated to reflux (oil bath about 120° C.). After 1.5 hours the reaction was filtered. The filtrate was cooled to about 4° C. and filtered. The white solid was dissolved in hot water treated with charcoal, filtered and treated with concentrated hydrochloric acid to produce a white precipitate. This was filtered, dried under vacuum at 80° C. for three hours to yield 3.3 g of 2,6-dihydroxy-9-phenylpurine (38% yield).

3.3 g of 2,6-dihydroxy-9-phenylpurine was added to a stirring suspension of 17 g PCl₅ in 83 ml POCl₃. The reaction was heated to reflux for 26 hours (oil bath 120° C.). After cooling, the solvent was removed under vacuum, the residue carefully quenched in ice water and the aqueous extracted with Et₂O (3 times, 200 ml). The combined organic extracts were dried over MgSO₄, filtered and concentrated to yield 3.52 g of product. After recrystallization from ethanol/water, this was dried under vacuum at 80° C. for 3 days to yield 1.40 g of 2,6-dichloro-9-phenylpurine.

1.24 g of 2,6-dichloro-9-phenylpurine was combined with 50 ml absolute ethanol, 0.7 ml triethylamine, 0.71 g of R(+)-2-amino-3-phenyl-1-propanol and heated to reflux for 5 hours. The solvent was then removed under vacuum and the residue purified by flash chromatography (5% methanol/trichloromethane) to yield 1.47 g of (R)-β-[(9-phenyl-2-chloro-1H-purin-6-yl)amino]benzenepropanol.

340 mg sodium was dissolved in 40 ml n-propanol. 1.4 g of (R)-β-[(9-phenyl-2-chloro-1H-purin-6-yl)amino]benzenepropanol was added and the reaction was heated to reflux for 4 hours. After cooling, the reaction was poured into about 200 ml 95% saturated sodium chloride solution and extracted with trichloromethane (3 times, 200 ml). The combined organic extracts were dried over MgSO₄, filtered and concentrated. The residue was purified by flash chromatography (2% methanol/trichloromethane) to yield 1.41 g of product. This was recrystallized from about 5% isopropyl alcohol/hexane to yield 1.05 g of impure product. 300 mg was again recrystallized from 5% isopropylalcohol/-hexane to yield, after drying under vacuum at 80° C. for 168 hours, 211 mg of (R)-β-[(2-propoxy-9-phenyl-1H-purin-6-yl)amino]benzenepropanol (m.p. 127°–128° C.).

750 mg of (R)-β-[(2-propoxy-9-phenyl-1H-purin-6-yl)amino]benzenepropanol was dissolved in 40 ml dry dichloromethane, treated with 0.95 ml SOCl₂ and heated to reflux for 3 hours. The solvent was then removed under vacuum and the residue purified by radial chromatography (5% methanol/trichloromethane). The product was then recrystallized from about 20% isopropyl alcohol/hexane to yield 180 mg of product. This was again purified by radial chromatography (3-6% methanol/trichloromethane, 2 mm plate) to yield a residue which was triturated with ether. The solid was collected and dried under vacuum at 39 C for 168 hours to yield 114.2 mg of product as a light brown solid. This was purified by radial chromatography (3-6% methanol/trichloromethane) to yield 60 mg of (R)-7,8-dihydro-3-phenyl-8-(phenylmethyl)-5-propoxy-3H-diimidazo[1,2-c:4

EXAMPLE 14

100 g of violuric acid was added to 1 liter of water with vigorous overhead stirring, and heated to 70° C. 200 g of sodium hydrosulfite was added in portions over 15 min. After 2.5 hours the reaction was filtered and the precipitate rinsed with water. The solid was dried under vacuum at 98° C. for 3 hours to yield 75 g of 5-amino-2,4,6-trihydroxypyrimidine.

75 g of 5-amino-2,4,6-trihydroxypyrimidine was dissolved in 1.5 to 5% sodium hydroxide with vigorous overhead stirring producing a violet solution. The reaction was heated to 60° C. and 63 ml phenyl isothiocyanate was added dropwise over 1.5 hours. The reaction turned pale yellow. The reaction was stirred an additional 2 hours at 60° C., cooled and acidified with glacial acetic acid producing a light yellow precipitate. This was filtered to yield about 75 g of N-(2,4,6-trihydroxy-5-pyrimidyl)-N'-phenylthiourea.

About 75 g of N-(2,4,6-trihydroxy-5-pyrimidyl)-N'-phenylthiourea was combined with 600 ml concentrated hydrochloric acid and heated to reflux for 5 hours (considerable foaming occurred). It was then diluted with 2 liters water and immediately filtered and washed with water. This was dried under vacuum at 80° C. for 2 days to yield 50.08 g of product (34% yield from violuric acid). A small sample was triturated with hot glacial acetic acid to yield 2,6-dihydroxy-9-phenyl-8-purinethiol.

2.5 g of 2,6-dihydroxy-9-phenyl-8-purinethiol was dissolved in 250 ml 1N sodium hydroxide and treated with 75 g Raney nickel. It was then heated to reflux for 2 hours and then filtered through Celite while hot. The filtrate was cooled to about 4° C., the white precipitate collected, dissolved in hot water, treated with charcoal, filtered, cooled in an ice bath and acidified with concentrated hydrochloric acid. The white product was collected and dried under vacuum at 70° C. for 2 days to yield 11.3 g of 2,6-dihydroxy-9-phenylpurine.

11.2 g of 2,6-dihydroxy-9-phenylpurine was combined with 280 ml POCl$_3$ and 57 g PCl$_5$ and heated to reflux (oil bath, 120° C.) for 24 hours. The solvent was then removed under vacuum and the residue quenched in ice. The aqueous was extracted with ether (4 times 500 ml), the combined organic extracts dried over MgSO$_4$, filtered and concentrated to yield about 4 g of product as a yellow solid. This was recrystallized form ethanol/water to yield 2.39 g of 2,6-dichloro-9-phenylpurine after drying under vacuum at 80° C. for 48 hours.

2.0 g of 2,6-dichloro-9-phenylpurine was combined with 1.15 g of S-(+)-2-amino-3-phenyl-1-propanol, 1.13 ml triethylamine and 70 ml absolute ethanol. The reaction was then heated to reflux for 4 hours. The solvent was then removed under vacuum and the residue purified by flash chromatography (3–5% methanol/trichloromethane) to yield 2.77 g of (S)-β-[(9-phenyl-2-chloro-1H-purin-6-yl)amino]benzenepropanol.

836 mg sodium was dissolved in 60 ml n-propanol. 2.76 g of (S)-β-[(9-phenyl-2-chloro-1H-purin-6-yl)amino]benzenepropanol, in 20 ml n-propanol, was added to the reaction and heated to reflux for 5 hours. After cooling it was poured into 200 ml 95% sodium chloride and extracted with trichloromethane (3 times, 200 ml). The combined organic extracts were dried over MgSO$_4$, filtered and concentrated to yield a residue which was purified by flash chromatography. This yielded 2.15 g of product. This was recrystallized from 5% isopropyl alcohol/hexane to yield after drying under vacuum at 70° C. for 24 hours 1.78 g of (S)-β-[(2-propoxy-9-phenyl-1H-purin-6-yl)amino]benzenepropanol (m.p. 126°–128° C.).

1.2 g of (S)-β-[(2-propoxy-9-phenyl-1H-purin-6-yl)amino]benzenepropanol was dissolved in 60 ml dry dichloromethane and treated with 1.53 ml SOCl$_2$. The reaction was heated to reflux under N$_2$ for 4 hours. The solvent was then removed under vacuum and the residue purified by flash chromatography (5% methanol/trichloromethane) to yield 0.99 g of product. This was dried under high vacuum at 39° C. for 7 days to yield 437.8 mg of (S)-7,8-dihydro-3-phenyl-8-(phenylmethyl)-5-propoxy-3H-diimidazo[1,2-c:4',5'-e[-pyrimidine (m.p. 74°–80° C.).

We claim:

1. A compound according to the formula:

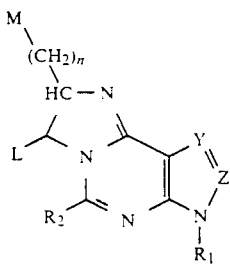

wherein
R$_1$ is hydrogen, phenyl or β-D-ribofuranosyl;
R$_2$ is hydrogen, lower alkyl of from 1 to 4 carbon atoms or lower alkoxy of from 1 to 4 carbon atoms;
Y is —N═ or —CH═;
Z is —N═ or —CH═, with the proviso that Y and Z are not identical;
n is an integer from 1 to 3;
L is hydrogen or phenyl; and
M is phenyl, except when L is phenyl, in which case M is hydrogen or a lower alkyl of from 1 to 3 carbon atoms.

2. A compound according to claim 1 of the formula:

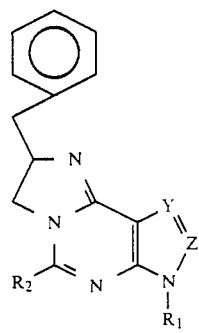

wherein
R$_1$ is hydrogen, phenyl or β-D-ribofuranosyl;
R$_2$ is hydrogen, lower alkyl of from 1 to 4 carbon atoms or lower alkoxy of from 1 to 4 carbon atoms;
Y is —N═ or —CH═;
Z is —N═ or —CH═, with the proviso that Y and Z are not identical.

3. A compound according to claim 1 of the formula:

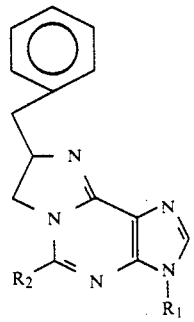

wherein R₁ is hydrogen, phenyl or β-D-ribofuranosyl; and R₂ is hydrogen, lower alkyl of from 1 to 4 carbon atoms, or lower alkoxy of from 1 to 4 carbon atoms.

4. A compound according to claim 1 which is (R)-7,8-dihydro-3-phenyl-8-(phenylmethyl)-3H-diimidazo[1,2-c:4′,5′-e]pyrimidine.

5. A compound according to claim 1 which is (S)-7,8-dihydro-3-phenyl-8-(phenylmethyl)-3H-diimidazo[1,2-c:4′,5′-e]pyrimidine.

6. A compound according to claim 1 which is (S)-7,8-dihydro-3-(β-D-ribofuranosyl)-8-(phenylmethyl)-3H-diimidazo[1,2-c:4′,5′-e]pyrimidine.

7. A compound according to claim 1 which is (R)-7,8-dihydro-3-(β-D-ribofuranosyl)-8-(phenylmethyl)-3H-diimidazo[1,2-c:4′,5′-e]pyrimidine.

8. A compound according to claim 1 of the formula:

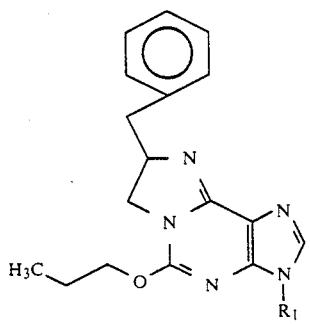

wherein R₁ is hydrogen, phenyl or β-D-ribofuranosyl.

9. A compound according to claim 1 which is (R)-7,8-dihydro-8-(phenylmethyl)-1H-diimidazo[1,2-c:4′5′-e]pyrimidine.

10. A compound according to claim 1 which is (S)-7,8-dihydro-8-(phenylmethyl)-1H-diimidazo[1,2-c:4′5′-e]pyrimidine.

11. A compound according to claim 1 of the formula:

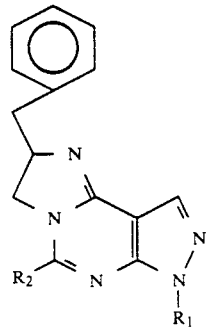

wherein R₂ is hydrogen, lower alkyl of from 1 to 4 carbon atoms or lower alkoxy of from 1 to 4 carbon atoms; and R₁ is hydrogen, phenyl or β-D-ribofuranosyl.

12. A compound according to claim 1 of the formula:

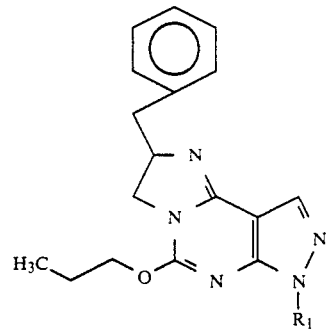

wherein R₁ is hydrogen, phenyl or β-D-ribofuranosyl.

13. A compound according to claim 1 which is (R)-2,7-dihydro-7-phenyl-2-(phenylmethyl)-5-propoxy-3H-imidazo[1,2-c]pyrazolo[4,3-e]pyrimidine.

14. A compound according to claim 1 which is (S)-2,7-dihydro-7-phenyl-2-(phenylmethyl)-5-propoxy-3H-imidazo[1,2-c]pyrazolo[4,3-e]pyrimidine.

15. A compound according to claim 1 which is (R)-2,7-dihydro-7-phenyl-2-(phenylmethyl)-3H-imidazo[1,2-c]pyrazolo[4,5-e]pyrimidine.

16. A compound according to claim 1 which is (S)-2,7-dihydro-7-phenyl-2-(phenylmethyl)-3H-imidazo[1,2-c]pyrazolo[4,5-e]pyrimidine.

17. A compound according to claim 1 of the formula:

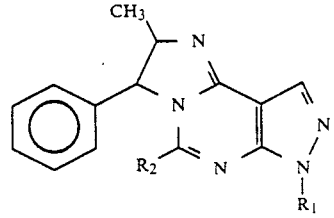

wherein R₁ is hydrogen, phenyl or β-D-ribofuranosyl; and R₂ is hydrogen, lower alkyl of from 1 to 4 carbon atoms or lower alkoxy of from 1 to 4 carbon atoms.

18. A compound according to claim 1 of the formula:

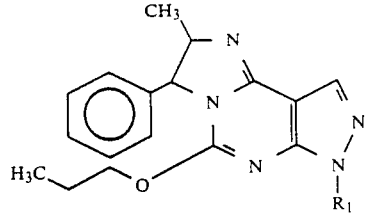

wherein R₁ is hydrogen, phenyl or β-D-ribofuranosyl.

19. A compound according to claim 1; which is (2R-trans)-2,7-dihydro-2-methyl-3,7-diphenyl-5-propoxy-3H-imidazo [1,2-c]pyrazolo[4,3-e]pyrimidine.

20. A compound according to claim 1 is (2S-trans)-2,7-dihydro-2-methyl-3,7-diphenyl-5-propoxy-3H-imidazo [1,2-c]pyrazolo [4,3-e]pyrimidine.

* * * * *